(12) United States Patent
Rigoulet

(10) Patent No.: US 6,644,971 B1
(45) Date of Patent: Nov. 11, 2003

(54) BIOLOGICAL MATERIAL FOR TREATING PERIODONTAL DISEASES

(76) Inventor: Franck Rigoulet, 760, Chemin des Vignasses, F-06410 Biot (FR)

( * ) Notice: Subject to any disclaimer, the term of this patent is extended or adjusted under 35 U.S.C. 154(b) by 135 days.

(21) Appl. No.: 09/700,935

(22) Filed: Nov. 20, 2000

Related U.S. Application Data

(63) Continuation of application No. PCT/FR99/02582, filed on Oct. 22, 1999.

(30) Foreign Application Priority Data

Oct. 23, 1998 (GB) .............................................. 9823307

(51) Int. Cl.⁷ ................................................ A61K 6/02
(52) U.S. Cl. ........................ 433/215; 424/423; 424/602
(58) Field of Search ................................ 424/422, 423, 424/602; 433/215

(56) References Cited

U.S. PATENT DOCUMENTS

| | | | |
|---|---|---|---|
| 4,976,736 A | * 12/1990 | White et al. ................... 623/16 |
| 5,618,549 A | * 4/1997 | Patat et al. .................. 424/422 |
| 5,681,872 A | * 10/1997 | Erbe ........................... 523/114 |
| 5,693,313 A | * 12/1997 | Shiraishi et al. ............... 424/49 |
| 5,711,957 A | 1/1998 | Patat et al. .................. 424/422 |
| 5,755,787 A | 5/1998 | Camprasse et al. ........... 623/11 |
| 5,807,554 A | * 9/1998 | Yng-Wong .............. 424/195.1 |
| 6,251,438 B1 | * 6/2001 | Lopez et al. ................. 424/547 |
| 6,376,573 B1 | * 4/2002 | White et al. ................. 523/115 |

FOREIGN PATENT DOCUMENTS

| FR | 2637502 | 4/1990 |
|---|---|---|
| WO | WO 94/17838 | 8/1994 |
| WO | WO 94/26283 | 11/1994 |
| WO | WO 97/46178 | 11/1997 |

* cited by examiner

*Primary Examiner*—Ralph A. Lewis
(74) *Attorney, Agent, or Firm*—James C. Lydon

(57) ABSTRACT

A biological material for treating periodontal diseases and all related disorders, the biomaterial comprising biocompatible bioaragonite, added calcium carbonate and optionally a binding agent. The bioaragonite is mother-of-pearl in micronised form. It is obtained by inhibiting the most immunogenic part of the bioaragonite organic substance so as to maintain bioactive only the organic part associated with the mineral capable of having a positive effect.

21 Claims, 9 Drawing Sheets

(9 of 9 Drawing Sheet(s) Filed in Color)

BIOLOGICAL MATERIAL FOR TREATING PERIODONTAL DISEASES

This application is a continuation of International application No. PCT/FR99/02582, filed Oct. 22, 1999, and now abandoned.

Technical field

The present invention concerns a biomaterial for treatment of periodontopathies and associated diseases, this biomaterial containing biocompatible bioaragonite.

STATE OF THE ART

Periodontopathies, or diseases affecting the periodontal region, can be of various origins such as genetic, infectious or traumatic.

In the present invention the term "bioaragonite" means nacre, preferably in a micronised form.

Nacre, also called "aragonite conchylifere" is in fact a biogenic mineralised formation essentially constituted of a mineral part consisting of calcium carbonate exclusively cryistallised as aragonite and also an organic matrix made up of fibrous and non fibrous substances corresponding to about 1% to 2% of the total mass. Nacre can be obtained from bivalve mollusc shells, especially some pearl oysters such as Pinctada maxima, of which it constitutes the innermost layer.

Document W090/14111 describes dental implants based on the inner layer of aquatic mollusc shells.

Similarly, "la nacre au service du squelette humain" (E. P. LOPEZ, S. BERLAND et A. LA FAOU, La Recherche 262, Fevrier 1994, Vol. 25, pages 208 to 210) describes an implant based on nacre, which is placed inside the jawbone and bio-integrated. A physiological reaction between the bone and the artificial dental root makes the tooth felt as a natural one.

An intervention allowing replacement of bone loss has also been described. It Consists in mixing nacre powder with a drop of the patient's own blood, to form a paste with which the bone gap is filled up. Such an intervention can be used for example in stomatology ("La nacre au secours des os; Nacre et stomatologie, l'alternative au dentier", Science et Avenir, Octobre 1994, P. 421.

However, such a intervention does not give satisfactory results because th filling material obtained (nacre powder mixed with blood) falls apart as soon as it is placed in the operating site. On the other hand, if pure nacre is used this can lead to an excessive bone forming stimulation, a result scientifically measured on animals.

SUMMARY OF THE INVENTION

The aim of the invention is to provide a biomaterial aimed to treat periodontopathies and associated diseases with which the above-mentioned drawbacks do not occur.

Accordingly to the present invention, the biomaterial comprises biocompatible bioaragonite, added calcium carbonate and, optionally a binder.

BRIEF DESCRIPTION OF THE DRAWINGS

The file of this patent contains at least one color photograph. Copies of this patent with color photograph(s) will be provided by the Office upon request and payment of the necessary fee.

DESCRIPTION OF THE INVENTION

Figure 1:
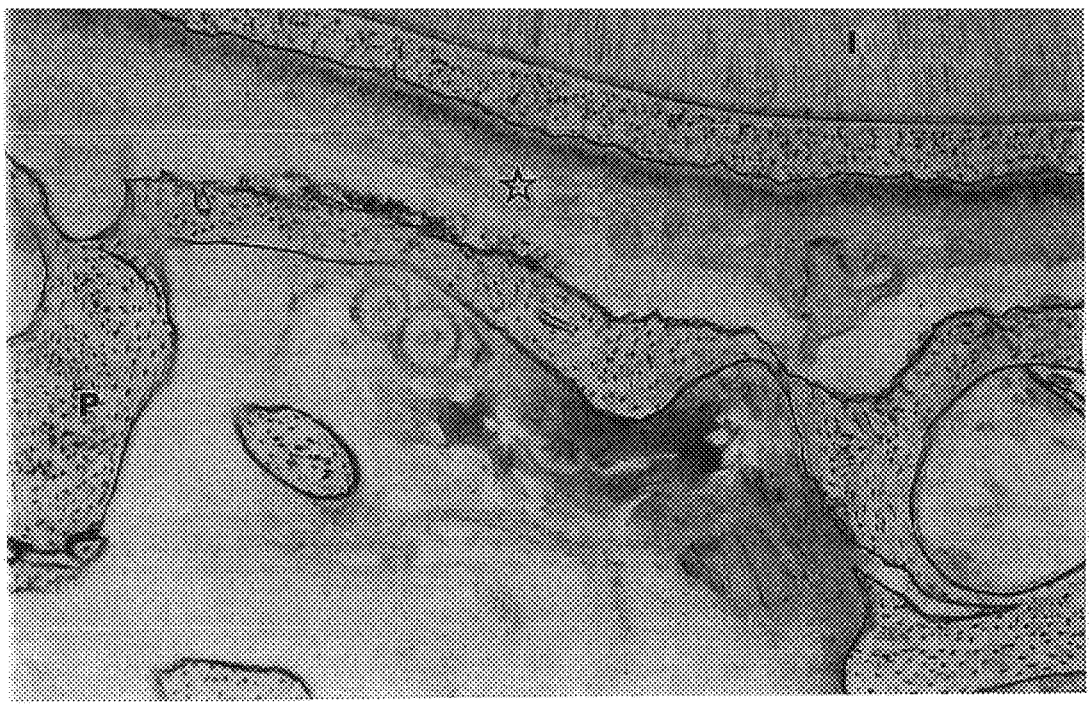
FIGS. 1 to 4 represent histological sections of parodontal bone and toothsocket ligament after induced parodontopathy.

Biocompatible bioaragonite is suitably present at a level ranging from 62 to 98% preferably from 70 to 90%, and more preferably from 75 to 85% compared to the total biomaterial weight.

Biocompatible bioaragonite may be obtained by inhibition of the most immunogenic part of the bioaragonite organic substance, in order to only maintain bioactive the part of the organic substances associated with its positive effect. The bioaragonite is thus rendered into a form having a reduced immunogenicity and being suitable for pharmaceutical use, referred to as biocompatible.

But the biocompatible bioaragonite obtained in this way can not be used as such to treat periodontopathies and related diseases.

The applicant has discovered that in fact clinical utilisation of this material is eased and made possible by addition of calcium carbonate to biocompatible bioaragonite.

The applicant nixes then this biocompatible bioaragonite with pure powdery calcium carbonate. This calcium carbonate can occur in a crystalline shape, as calcite (orthorhombal calcium carbonate) or as aragonite (rhombohedral calcium carbonate) or even in an amorphous form. This calcium carbonate addition allows mixing of the biocompatible bioaragonite paste with blood added afterwards. Besides, the step of mixing biocompatible bioaragonite (essentially made up of pure crystalline calcium carbonate orthorhombal shape) with pure calcium carbonate allows excessive bone regrowth to be avoided. The use of biocompatible bioaragonite alone would lead to such a drawback. The calcium carbonate added in embodiments of the invention represents 2 to 38% of the total weight, preferably ranging from 10 to 30% and more preferably 15 to 25% compared to the biomaterial total weight. The mixing of biocompatible bioaragonite and added calcium carbonate may be conducted in a mixer, then the mixture autoclaved for 15 to 20 minutes at a temperature of 100 to 120° C. The mixture is then stored in sterile bags or sterile flasks in order to avoid any exogenous contamination.

The implementation of the invention (the administration of the biomaterial to the patient) needs to combine the mixture of biocompatible bioaragonite and calcium carbonate with a number of additional adjuvant.

To this complex of biocompatible bioaragonite and calcium carbonate, can be added a binder, which may be present in a ratio ranging front 60 to 150% of the biomaterial total weight, preferentially the ratio must reach 70 to 120%, and more preferentially 80 to 100%. This binder is preferentially selected from hyaluronic acid, chondroitine sulphuric acid, guar gum, alginate, xanthan gum or collagen, and particularly marine collagen. This binder prevents the complex of biocompatible bioaragonite and added calcium carbonate from breaking down when in contact with blood in or around the operating site.

To this complex may also be added a plasticizer, made from a biocompatible substance able to produce a homogenous complex permeable to biological circulating liquids. This plasticizer is added in various quantities according to the practitioner's choice in order to obtain a more or less hard paste. Preferentially, this plasticizer consists of patient's own blood. This blood is withdrawn with a sterile syringe from the operating site, in the spongious bone lacunas which constitute the parodonte or preferentially intravenously. This plasticizer facilitates the production of a homogenous paste which does not fall apart when introduced in the proper site and is permeable to circulating liquids.

A hardener can also be added. This hardener is added in various quantities depending on the practitioner's choice to obtain a faster or slower hardening. This hardener allows solidification of the homogenous complex introduced into the affected site as described. If the patient's own blood has been selected as plasticizer, it will also act as a hardener.

A controlled denaturation of the bioaragonite may be performed using the innermost layer of a bivalve mollusc shell as starting material, preferentially in the form of tablets 2 to 5 cm long and 0. 3 cm thick.

This starting material is first decontaminated, oxidised and washed. These operations are operated inside inert heatable containers. The starting material is first brought to a boil with demineralised water for approximately one hour, then the decontaminating liquid is added in a suitable proportion of ¼ of the mass (¼ of decontaminating liquid to ¾ of water). This decontaminating liquid consists preferentially of an antiseptic and oxidative mixture comprising sodium hypochlorite at 6.6% of active chlorine in an aqueous solution. The solution is kept boiling for several hours and stirred regularly. The starting material is then very carefully rinsed and stirred under water until total elimination of the decontaminating liquid and any impurities is completed.

The starting material is then rinsed with demineralised water and undergoes several successive boiling and rinsing steps.

The starting material thus becomes biocompatible since the most immunogenic part of the organic substance has been inactivated during the oxidative decontamination process.

During a second step, the biocompatible starting material obtained as described above may be dried in a controlled atmosphere at about 100° C.

During the following step, the dried biocompatible starting material obtained is stored in sterile plastic bags. Then, it is cracked inside the bags and crushed until reduction to powder is achieved. The crushing is done in specific containers exclusively kept for this purpose.

The powdery biocompatible starting material (that will be called from now on biocompatible bioaragonite) obtained is stored in plastic bags, of Poupinel type, allowing the last washing phase.

The biocompatible bioaragonite is washed several times in the bags with distilled water, then dried in Pasteur oven. It is then reduced into powder by crushing with a mallet.

The efficiency of a biomaterial according to the invention for treatment of periodontopathies and related diseases is described further in the following experimentation results and illustrated by FIGS. 1 to 14 which show tissues histological sections, in which (P) corresponds to parodontal bone, (L) corresponds to toothsocket ligament, (I) corresponds to ivory and (N) corresponds to nacre particles.

Samples are withdrawn on dogs teeth showing periodontal lesions experimentally induced and treated with the biomaterial according with the invention and non treated animals (control group).

Periodontal means tissues, which surround the tooth and constitute its support: parodontal bone, tootheocket ligament and cement.

Samples are treated according to techniques used for mineralised tissues histological study without preliminary demineralisation.

The three tissues forming the periodontal, i.e. parodontal bone, toothsocket ligament and cement have been dealt with in an elaborate optical microscopy study.

The parodontal bone constitutes the alveolus wall. It is a spongy type bone.

The parodontal bone of a tooth showing an induced periodontopathy is characterised by an important degeneration showed by wide decayed endo-osseous crypts instead of the small active lacunas found in healthy cancellous bone of this type.

Figure 2:
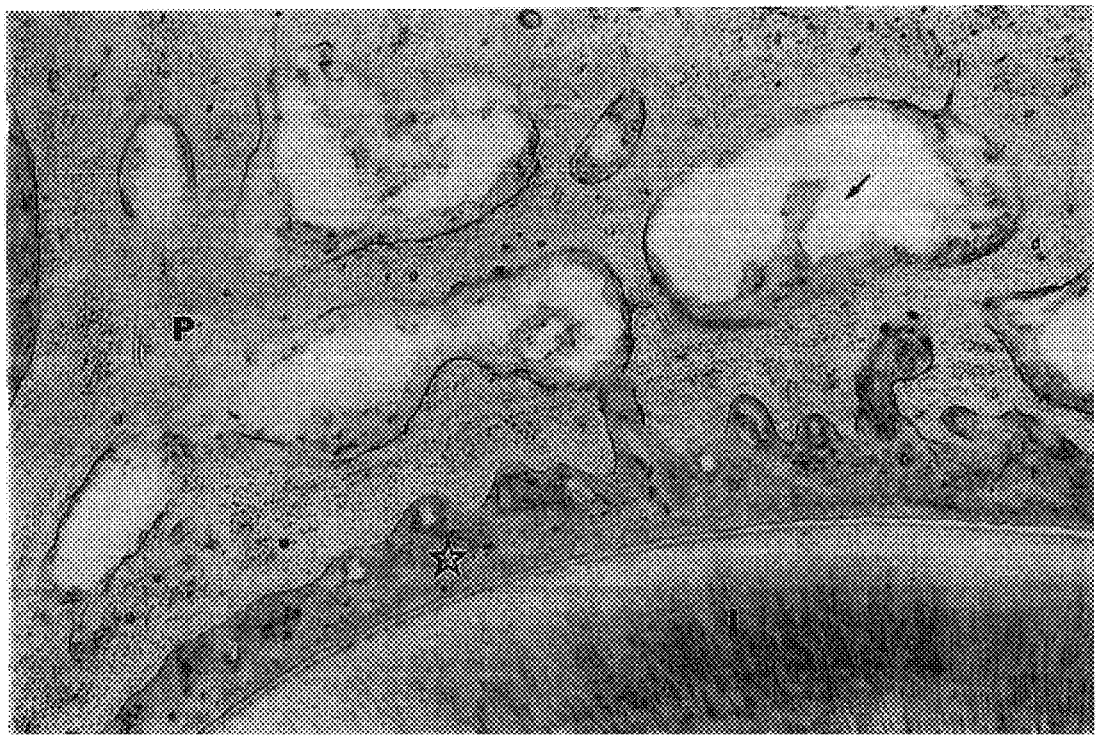
Figure 3:
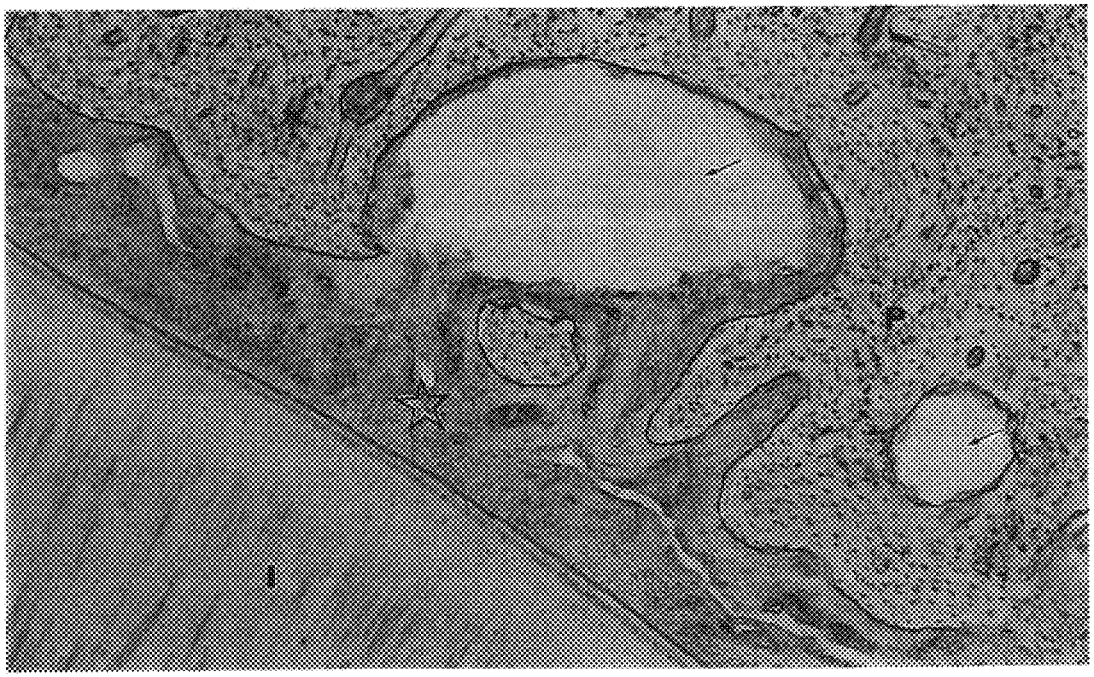
Figure 4:

The resorption crypts in contact with the toothsocket ligament are numerous and abnormally widened. This bone presents a lack of remodelling active units, which characterise a physiologically healthy bone. The functional physiological relation between the alveolus wall, the ligament and the root coating where the cement is, poor or absent does not exist anymore. The Sharpey fibres bundles binding the tooth to the parodontal bone have disappeared and are replaced by numerous fibrous disorganised islets. Those observations are illustrated in FIGS. 1 to 4. In FIG. 1, we can observe a lesion (☆) induced to the parodontal bone and a lack of toothsocket ligament. In FIG. 2, we can observe a disorganised toothlsocket ligament (☆) and an abnormally vacuolar parodontal bone. Vacuoles are characterised by an absence of cells population (→) In FIG. 3, we can observe enlarged resorption crypts (→) on parodontal bone level and a disorganized ligament (☆). In FIG. 4, we can observe details of the resorption crypts (☆) filled with pyenotic cells population on paradodontal bone level. We can also observe cancellous bone islets (→).

Figure 7:
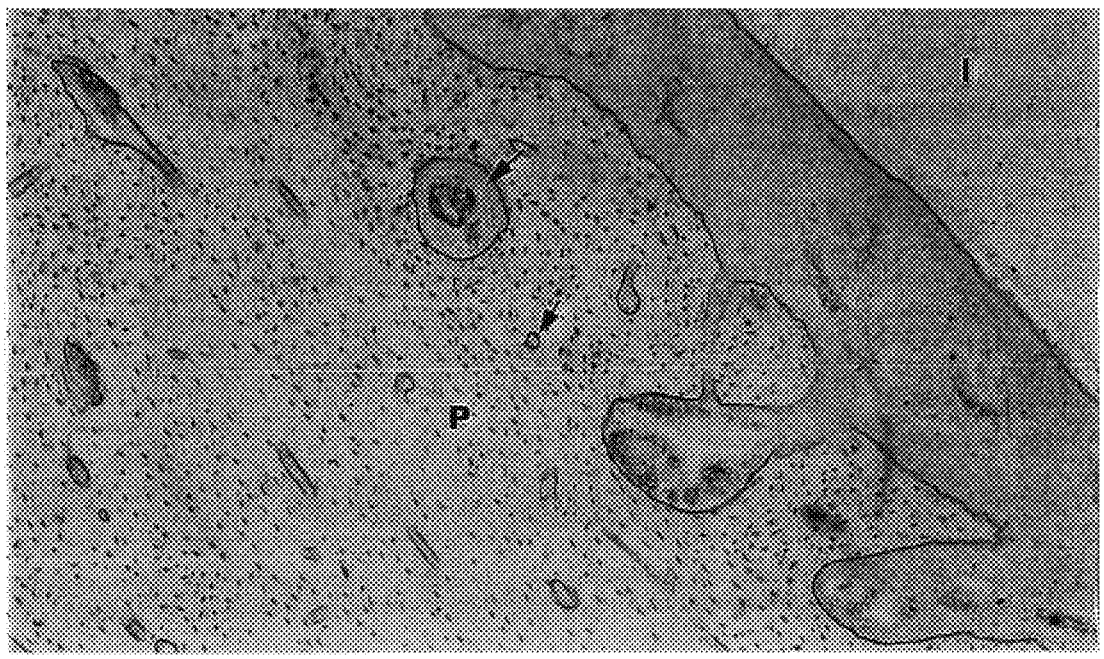
FIGS. 7 and 8 represent histological sections of parodontal bone after induced parodontopathy and treatment with the biomaterial according to the invention.
Figure 8:
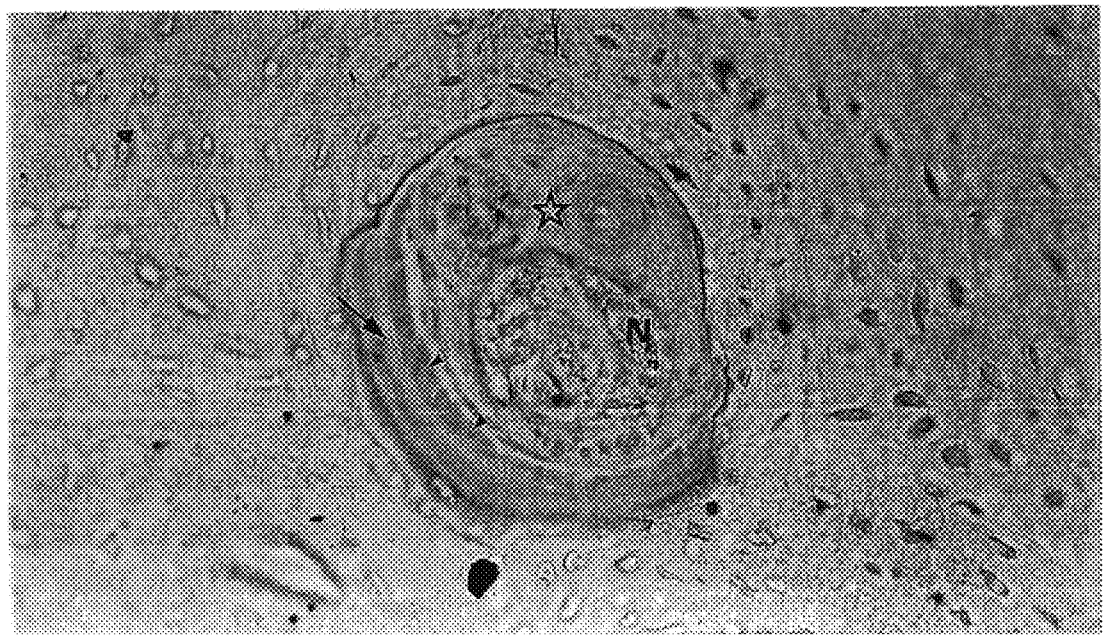
Figure 9:
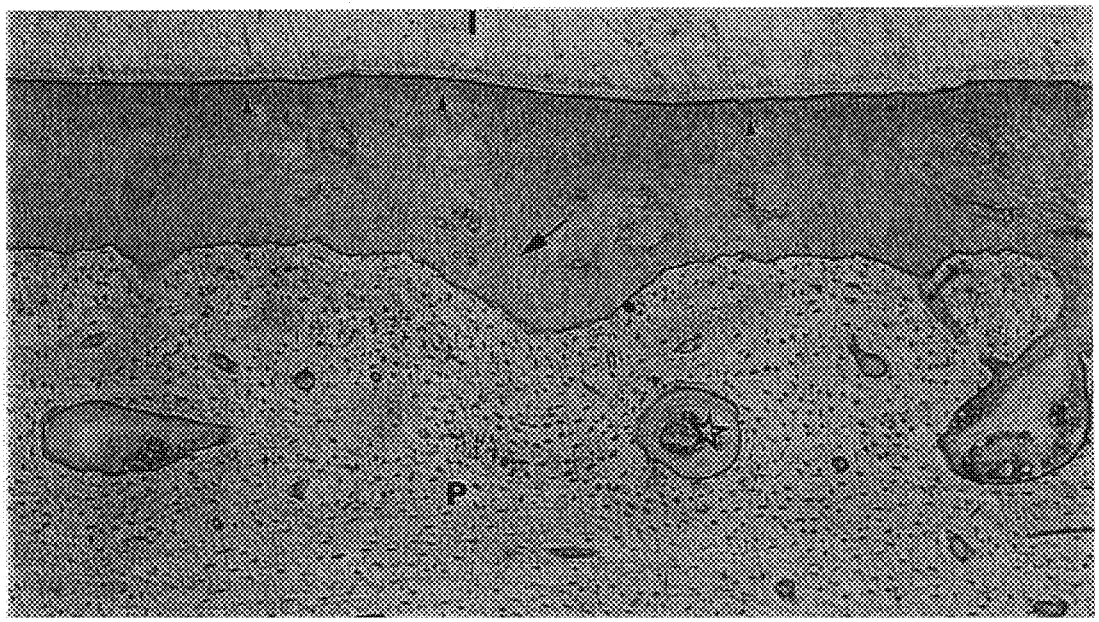
FIGS. 9 and 10 represent histological sections of parodontal bone and toothsocket ligament after induced parodontopathy and treatment with the biomaterial according to the invention.
Figure 10:
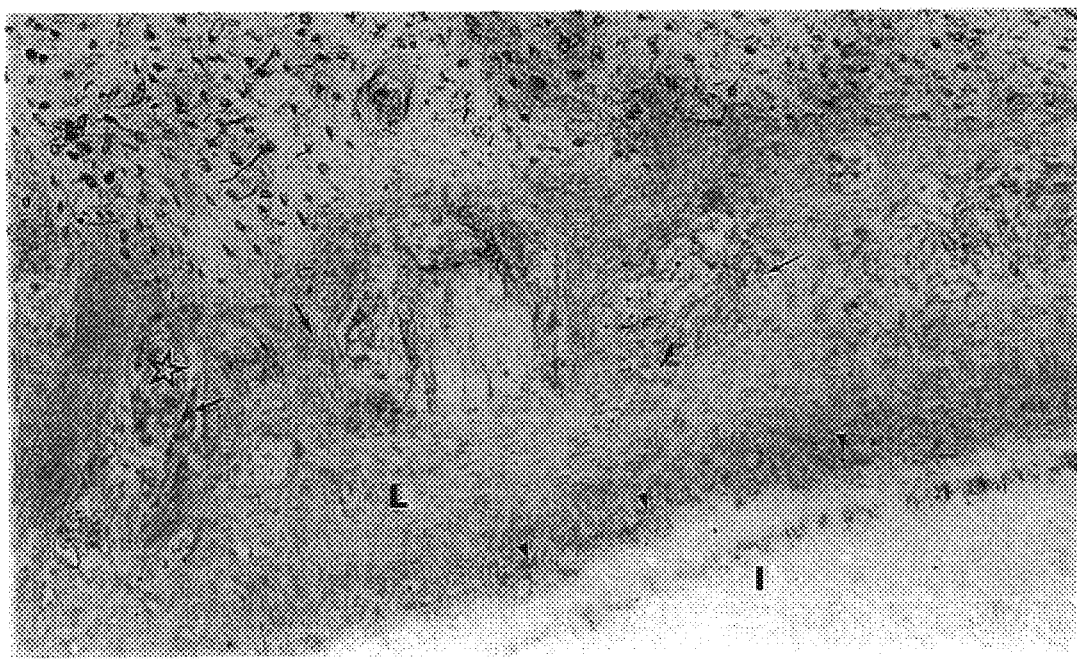

The parodontal bone of a tooth treated with the biomaterial according to the invention presents no more degenerative crypts. The latter are restructured by new bone formation. The bone has a regularly lamellar structure that gives evidences of its physiological maturity and is the site of active remodelling. The remodelling units are edged by very active bone forming cells (osteoblasts) and by bone undergoing a mineralisation process revealing the new bone formation. A perfect cellular cohesion can be observed between the alveolar bone wall and the cement-enriched root. The disorganised fibrous islets have disappeared and are replaced by Sharpey fibres bundles, which restore the link from the tooth to the parodontal bone. This cohesion gives a histo-structural aspect that demonstrates the bone integrity and specially the active part played by one of its elements the toothsocket ligament. These observations are well illustrated in FIGS. 7 to 10. In FIG. 7, parodontal bone is the site of active remodelling (→). In FIG. 8, we can observe the detail of a functional remodelling unit (☆)

organised around nacre fragment undergoing a biodissolution. We can notice the significant osteoid border (→) undergoing a mineralisation process, evidences of new tone formation and activated osteoblasts (▶). In FIG. 9, parodontal bone is the site of active remodelling (☆). We can notice a clear organisation on the toothsocket ligamenl level, Sharpey fibres bundles anchored on parodontal bone and the cement (☆), an edge of activated cells rebuilding the cement (▶). In FIG. 10, we can observe in detail the physiological quality of the parodontal bone and the toothsocket ligament. We notice activated fibroblasts, Sharpey fibres (→), in contact with nacre particles undergoing biodissolution (☆), and a border of active camentoblasts.

About the toothsocket ligament and the cement, a healthy toothsocket ligament is formed by a dense fibrous connective tissue binding the root to the bone alveolus (parodontal bone). The root ivory is covered by a lamella of cement synthesised by a layer of cells: the cementoblasts, which once trapped in the physiologically active cement are transformed into cementocytes situated in the lacunas. The cement is not very different from bone. It plays a major role. In fact, collagen fibres from the toothsocket ligament are bundled up and called Sharpey fibres. These bundles start from the parodontal wall to anchor in the cement. The healthy toothsocket ligament is rich in blood vessels and nervous fibres. Heaps of epithelial cells support the Sharpey fibres path. They constitute the Malassez corpuscles.

Figure 5:
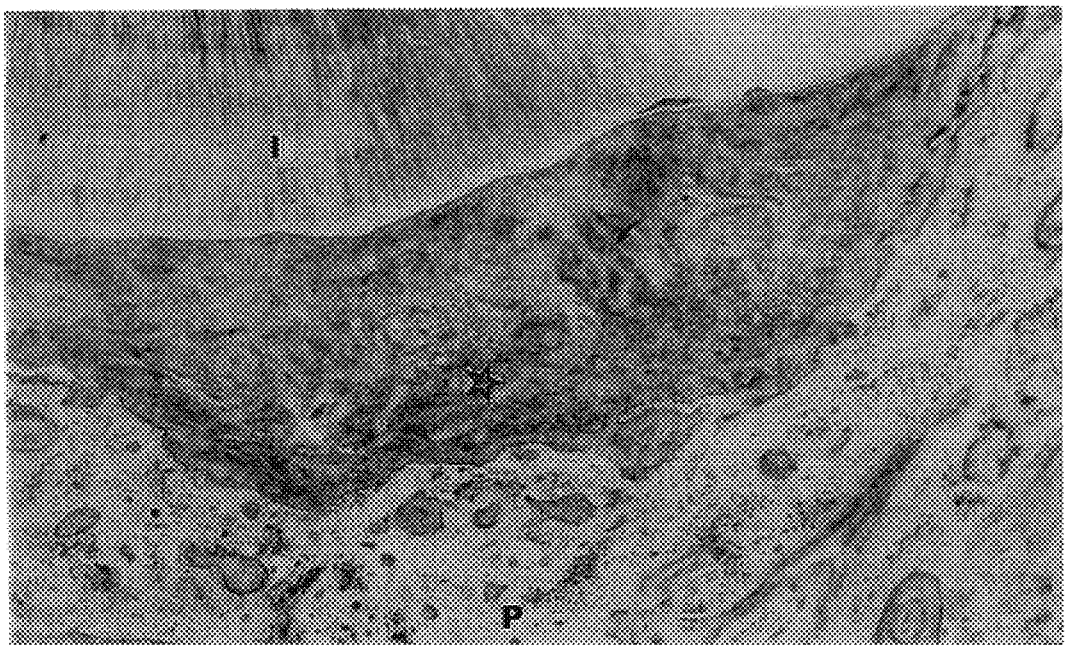
FIGS. 5 and 6 represent histological sections of toothsocket ligament after induced parodontopathy.
Figure 6:
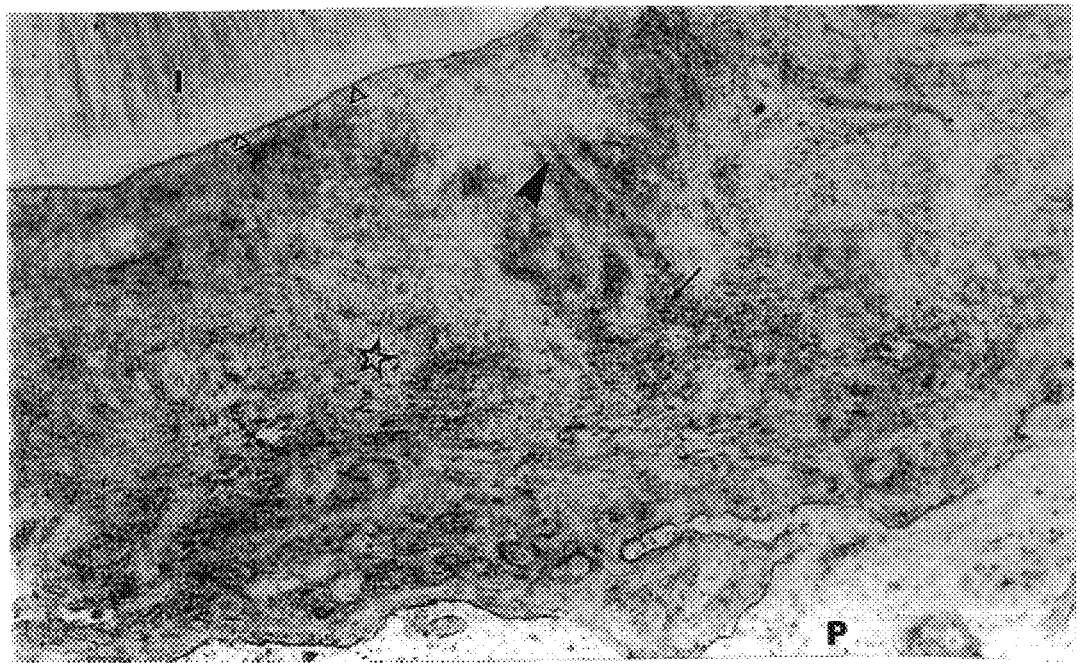

Concerning the toothsocket ligament and the cement of a tooth altered by a periodontal disease, we can observe that the toothsocket ligament is in some part non-existent, i.e. totally lysed. When remaining, it is formed by a heterogeneous tissue the components of which are difficult to identify. The fibroblasts are degenerating. The blood irrigation is non-existent. The Sharpey bundles are disorganized and have no attachment points neither on the parodontal bone nor on the cement, which is practically non-existent. The total lack of active cementoblasts can be noticed. Those observations are well illustrated in FIGS. 5 and 6. In FIG. 5, we can observe disorganized ligament (☆) composed of heterogeneous connective tissue. Sharpey fibres are without attachment point (→)In FIG. 6, we observe a detail of the disorganised toothsocket ligament (☆), pyenotic fibroblasts (→), Sharpey fibres without attachment point (▶), a thin cement layer and absence of active cementoblasts (▶).

Figure 11:
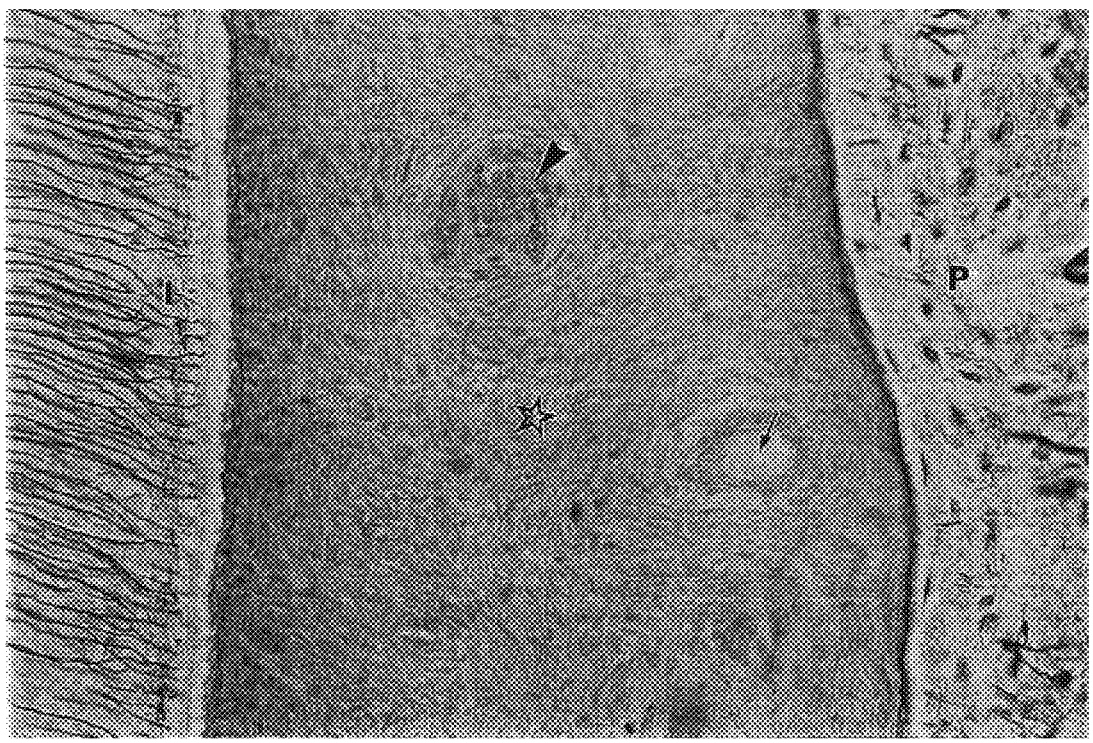
FIG. 11 represents a histological section of toothsocket ligament after induced parodontopathy and treatment with the biomaterial according to the invention.
Figure 12:
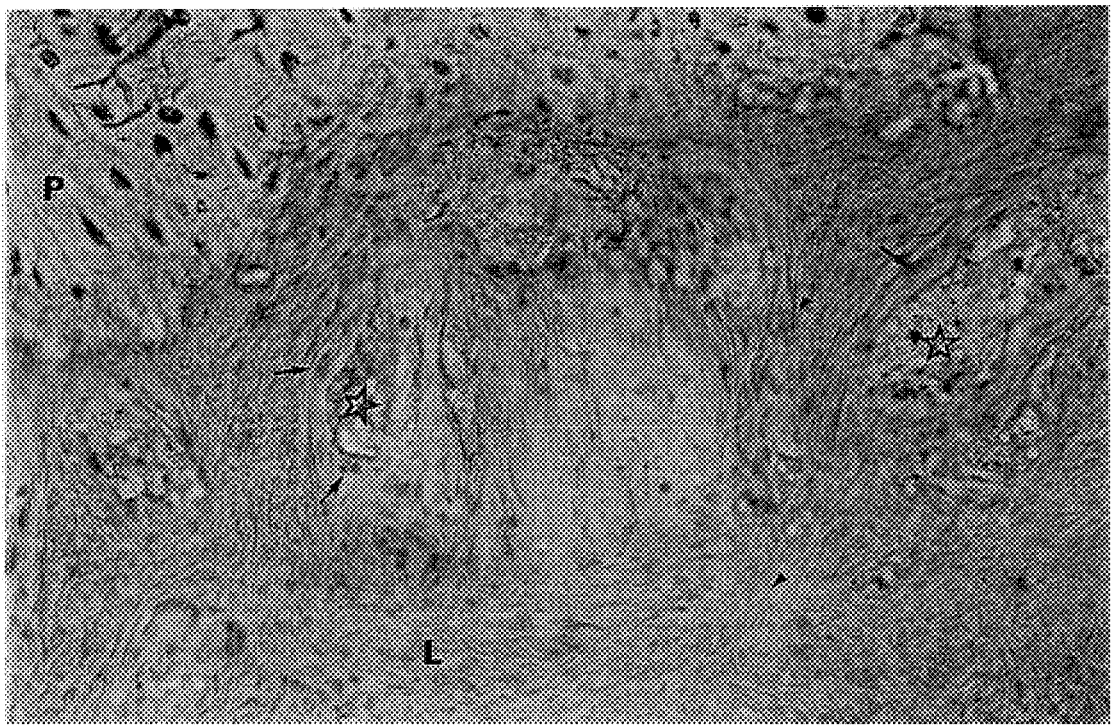
FIGS. 12 and 13 represent histological sections of the parodontal bone/toothsocket ligament interface after induced parodontopathy and treatment with the biomaterial according to the invention.
Figure 13:
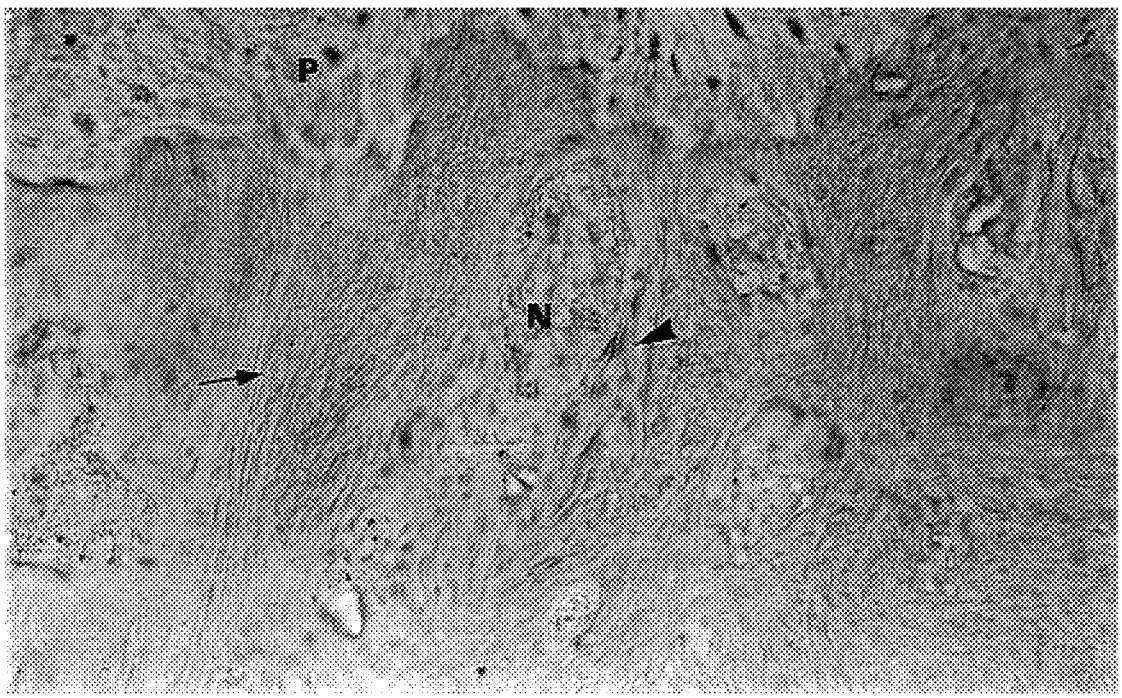
Figure 14:
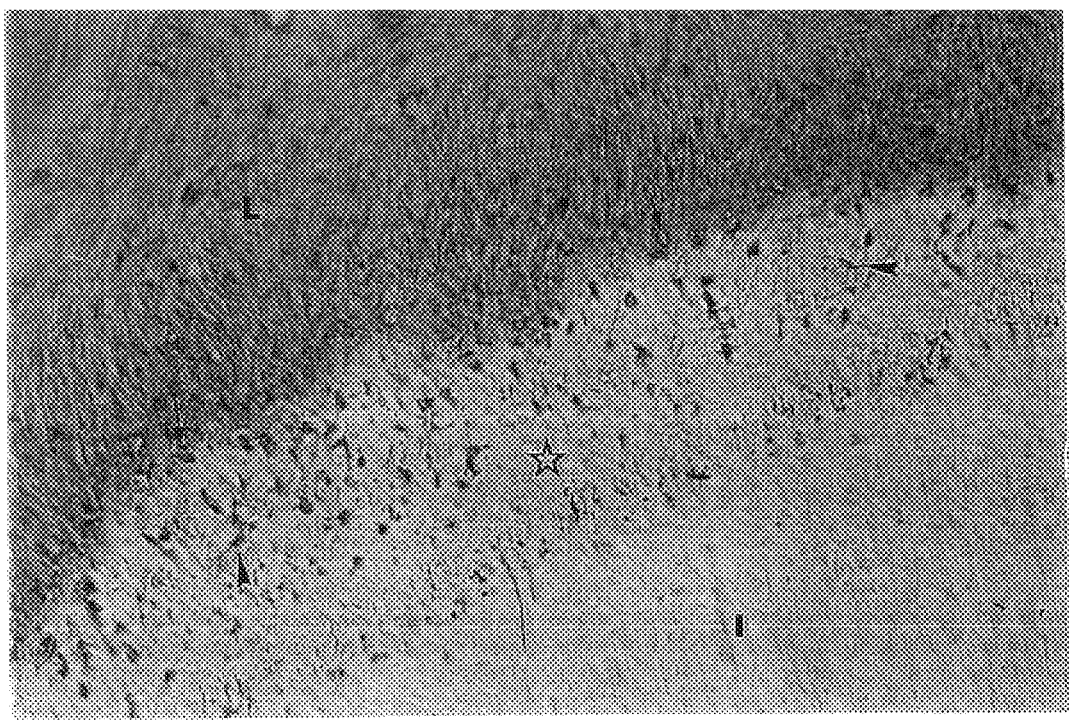
FIG. 14 represents a histological section of cement at the tooth/toothsocket ligament interface after induced parodontopathy and treatment with the biomaterial according to the invention.

On the other hand, concerning the toothsocket ligament and the cement of a tooth treated with the biomaterial according to the invention as shown in FIGS. 11 to 14, the regenerated active osteocyte-rich parodontal bone dispatches wide Sharpey fibres bundles which anchored on newly formed cement layer. A zone of active cementoblasts and cementocytes-rich cement can be observed in perfect physiological cohesion with underlying dentine. The fibroblasts are very stimulated as proved by their clear, swollen nucleus, this is more specially near the residual particles issued from biomaterial implantation and undergoing a biodissolution process. The toothsocket ligament is rich in blood vessels and Malassez corpuscles surrounded by Sharpey fibres. FIG. 11 shows physiological quality of the tissues: blood vessels (→). We observe the Malassez corpuscles (▶) and active cemantoblasts (▶). FIG. 12 shows fibroblasts activation (→), in contact with nacre particles undergoing a biodiassolution process (☆) We can also observe numerous Sharpey fibre bundles (▶). FIG. 13 shows the Sharpey fibre organisation (→), Sharpey fibre bundles anchored on the parodontal bone, near the nacre particle undergoing a biodissolution process and activated fibroblasts (▶). In FIG. 14, we can observe in detail the border of active cementoblasts (→) wind the cementocytes (▶) trapped inside the newly formed layer (☆).

Those experiments then lead to the conclusion that the treatment of periodontal diseases with a biomaterial according to this invention induces a restructuring of the parodontal bone and stimulation of its activity, a cementoblasts and cementocytes stimulation accompanied with an increased synthesis of cement, and a functional regeneration of the toothsocket ligaments particularly Sharpey fibres and their connecting point parodontal bone/cement.

These various effects allow the complete restoration of the tooth functional activity within its alveolus.

What is claimed is:

1. A material for treatment of periodontopathies and related diseases, comprising:
   biocompatible bioaragonite, and
   pure calcium carbonate having either a crystalline shape or an amorphous form,
   wherein the biocompatible bioaragonite is constituted by a bivalve mollusc shell innermost layer in a powdery or micronized form, of which the most immunogenic part has been substantially inactivated.

2. The material of claim 1, further comprising a binder.

3. The material of claim 2, wherein said binder is at least one member selected from the group consisting of hyaluronic acids chondroitine sulphuric acid, guar gum, alginate, xanthan gum and collagen.

4. The material of claim 2, wherein the binder is present in an amount ranging from 60% to 150% in weight compared to the combined weight of the bioaragonite and the pure calcium carbonate.

5. The material of claim 4, wherein the binder is present in an amount ranging from 70 to 120%.

6. The material of claim 5, wherein said binder is present in an amount ranging from 80 to 100%.

7. The material of claim 1, wherein the biocompatible bioaragonite in micronized form.

8. The material of claim 1, wherein the biocompatible bioaragonite is obtained by means of a controlled denaturation of the bivalve mollusc shell inner layer such that the most immunogenic part of its organic content is inactivated and that part of its organic content associated with the mineral able to have a positive effect is essentially preserved, and wherein the bioaragonite is rinsed, dried and crushed until it has a powdery form.

9. The material of claim 8, wherein said controlled denaturation comprises oxidation of the most immunogenic part of the organic content of the inner layer with hypochlorite.

10. The material of claim 1, wherein the pure calcium carbonate is present in a powdery form.

11. The material of claim 1, wherein the biocompatible bioaragonite is present in an amount ranging from 62 to 98% in weight compared to the total weight of the material.

12. The material of claim 11, wherein said biocompatible bioaragonite is present in an amount ranging from 70 to 90%.

13. The material of claim 12, wherein said biocompatible bioaragonite is present in an amount ranging from 75 to 85%.

14. The material of claim 1, wherein the pure calcium carbonate is present in an amount ranging from 2 to 38% in weight compared to the total weight of the material.

15. The material of claim 14, wherein said pure calcium carbonate is present in an amount ranging from 10 to 30%.

16. The material of claim 15, wherein said pure calcium carbonate is present in an amount ranging from 15 to 25%.

17. A method of treatment of periondotonpathies or related diseases, comprising administering an effective amount of the material of claim 1 to a mammal in need of said treatment.

18. The material of claim 1, wherein said pure calcium carbonate has an orthorhombic crystalline structure.

19. A method for preparing a bioaragonite containing composition for treatment of periondotonpathies and related diseases, comprising extracting a bivalve mollusc shell innermost layer, substantially inactivating the most immunogenic part of said extracted layer, crushing the said layer until it has a powdery or micronized form, with the resulting product constituting biocompatible bioaragonite mixing said biocompatible bioaragonite with pure calcium carbonate having a crystalline shape or an amorphous form.

20. The method of claim 19, further comprising mixing said bioaragonite and pure calcium carbonate with a binder.

21. The method of claim 20, wherein 62 to 98% of biocompatible bioaragonite is mixed with 38 to 2% of pure calcium carbonate.

* * * * *